United States Patent [19]
Hirschkoff et al.

[11] Patent Number: 5,506,200
[45] Date of Patent: Apr. 9, 1996

[54] COMPACT SUPERCONDUCTING MAGNETOMETER HAVING NO VACUUM INSULATION

[75] Inventors: Eugene C. Hirschkoff, Leucadia; Mark S. DiIorio; Richard T. Johnson, both of San Diego; D. Scott Buchanan, Escondido, all of Calif.

[73] Assignee: Biomagnetic Technologies, Inc., San Diego, Calif.

[21] Appl. No.: 831,905

[22] Filed: Feb. 6, 1992

[51] Int. Cl.[6] ............................................. G01R 33/035
[52] U.S. Cl. ...................... 505/162; 324/248; 505/846
[58] Field of Search ........................ 324/248; 505/845, 505/846; 62/64; 128/653.1

[56] References Cited

U.S. PATENT DOCUMENTS

| | | | |
|---|---|---|---|
| 3,916,248 | 10/1975 | Nicol | 324/248 |
| 3,980,076 | 9/1976 | Wikswo, Jr. et al. | 324/248 |
| 4,700,135 | 10/1987 | Hoenig | 324/248 |
| 4,715,189 | 12/1987 | Hohenwarter | 62/64 |
| 4,827,217 | 5/1989 | Paulson | 324/248 |
| 4,982,158 | 1/1991 | Nakata et al. | 324/248 |
| 5,004,724 | 4/1991 | De | 324/248 |
| 5,166,614 | 11/1992 | Yokosawa et al. | 324/248 |

Primary Examiner—Walter E. Snow
Attorney, Agent, or Firm—Gregory Garmong

[57] ABSTRACT

A magnetometer comprises a magnetic field pickup coil and a magnetic field detector that receives electrical signals from the pickup coil and produces an electrical detector output responsive thereto. The pickup coil and detector, which are preferably made of high temperature superconductors, are enclosed in an insulated enclosure having no vacuum insulation structure. Preferably, the enclosure is made of a foamed polymer material such as styrofoam. A coolant is provided to the interior of the enclosure, to cool the pickup coil and detector to a temperature below their superconducting transition temperature. A number of such modular magnetometers may be connected together to form an array.

21 Claims, 5 Drawing Sheets

COMPACT SUPERCONDUCTING MAGNETOMETER HAVING NO VACUUM INSULATION

BACKGROUND OF THE INVENTION

This invention relates to devices for detecting magnetic fields, and, more particularly, to a compact, highly sensitive magnetometer using high temperature superconductors.

A magnetometer, as the term is used herein, is a device for detecting changes in magnetic fields. The most sensitive magnetometers presently available for relatively low frequencies include a pickup coil which produces a change in an electrical signal responsive to a change in a magnetic field. The pickup coil is typically made from a material such as niobium that becomes superconducting below about 10 K. The electrical signal is detected by a Superconducting Quantum Interference Device (known by its acronym, SQUID), also typically made from niobium, that can detect the very small electrical signals produced by a small magnetic field change. Recently, SQUIDs made of high critical temperature (high-Tc) oxide ceramics have been fabricated, tested, and found operable.

Biomagnetometry, the measurement and study of magnetic fields produced by the human body, is one of the most demanding applications of magnetometers. The biomagnetometer uses magnetometers placed external to the body to measure extremely small magnetic fields produced by a source organ within the body, such as the brain or the heart. A typical biomagnetometer utilizes a sensitive superconducting magnetometer such as that described previously, placed within a dewar vessel to maintain the magnetometer below its superconducting critical temperature.

In a presently available commercial biomagnetometer, the dewar is cylindrical, about 4 feet long by 18 inches in diameter, and weighs about 80 pounds. The pickup coil is placed within a small appendage or "dewar tail" extending from the bottom of the main vessel, which contains the SQUID detector. The dewar is essentially a well-insulated vacuum bottle filled with liquid helium or, in some cases, cooled to liquid helium temperatures by a mechanical cooler. The presently available biomagnetometers require large gantry mechanisms to suspend them adjacent to the subject. Even then, the biomagnetometers are limited in their placement adjacent to the subject. The results attained with the currently available biomagnetometers could be improved if the pickup coil could be placed closer to the body of the subject, and if multiple pickup coils could be provided in configurable arrays.

There is a need for an improved magnetometer of very high sensitivity, operable for biomagnetometry and other applications, that is smaller and lighter than existing magnetometers. Such a magnetometer would desirably be more readily used in arrays and would be less costly to manufacture and operate. The present invention fulfills this need, and further provides related advantages.

SUMMARY OF THE INVENTION

The present invention provides a magnetometer module that utilizes a superconducting pickup coil and SQUID detector, yet is so compact that, in one embodiment, the magnetometer module easily fits within the palm of the hand. The magnetometer is therefore sensitive, yet can be used in applications that are impossible for the conventional superconducting magnetometer because of its size and weight. A number of the modular magnetometers of the invention may be used together in an array that improves system sensitivity even further. The present magnetometer is also potentially far less expensive to build and operate than the conventional magnetometer, and offers wider opportunities for commercial use.

In accordance with the invention, a magnetometer comprises a magnetic field pickup coil and a magnetic field detector that receives electrical signals from the pickup coil and produces an electrical detector output responsive thereto. The pickup coil and detector, which are preferably made of high temperature superconductors, are enclosed in an insulated enclosure having no vacuum insulation structure. Preferably, the enclosure is made of a foamed polymer material such as styrofoam. A coolant is provided to the interior of the enclosure, to cool the pickup coil and detector to a temperature below their superconducting transition temperatures. A number of such modular magnetometers may be connected together to form an array.

The pickup coil and the detector are made from superconducting materials whose critical temperatures are above about 77 K. The critical temperature, Tc, of a material is the temperature below which it becomes superconducting in the absence of an applied magnetic field or applied current. An applied magnetic field or applied current reduces the temperature at which the material becomes superconducting. Since the magnetic fields and associated currents for magnetometer applications are so small compared to the values which might affect the superconducting transition temperature, identification of the superconducting materials of the invention in terms of their critical temperatures is an excellent approximation. Because the Tc values of the superconducting materials used in the pickup coil and detector of the magnetometer of the invention are above about 77 K, they can be cooled with liquid nitrogen, cold nitrogen gas, some other relatively inexpensive, long-lasting coolant, or a cryocooler such as one of the gas-expansion type. Cryocoolers of the latter type designed for operation at 77 K or above are much more reliable and less expensive than those which operate at lower temperatures.

A key feature of the present invention is the recognition that the use of electrically active components having Tc values above about 77 K permits the elimination of a vacuum-bottle type dewar vessel. Instead, the superconducting pickup coil and the superconducting detector may be enclosed within a non-vacuum insulator container made of a material such as an insulative foam and/or layered mylar. With a continuous flow of coolant through the enclosure, the insulation enclosure may be made relatively thin and compact.

In a preferred approach, the pickup coil and the SQUID detector are made of an available high-temperature oxide ceramic superconductor (but are not so limited) and are supported on a single substrate less than about 1–2 inches square, which has very little thermal mass. The substrate is placed into a hollow block of foam whose walls have a thickness of as little as about 1/8 inch. The foam block can be coated with an impenetrable layer to prevent any leakage of cryogenic gas to the subject being measured. A slow flow of cryogenic nitrogen or argon gas cools the interior of the foam block, and thence the pickup coil and SQUID. Leads to external ambient temperature SQUID electronic circuitry extend from the substrate and through the foam block. By way of example, the magnetometer of this approach can be made with overall dimensions as small as about 1 inch by 1 inch by ½ inch thick and weighing only a few ounces, or even smaller if the pickup coil is made smaller. The foam block can be held in the hand even when the magnetometer is operating, and placed so that the pickup coil is no more than about 1/8 inch from the surface from which the magnetic field is emitted.

A number of the compact magnetometers of the invention, being modular in form, are readily used together with other modular magnetometers of the same type (and with the same or differing types of pickup coils) to form a magnetometer array. The array can be flexible in form to accommodate to an irregular shape, or held in a rigid arrangement. The information derived from such arrays can be processed to gain a much greater understanding of the magnetic field sources than possible with the magnetometers presently available or with single magnetometers.

The magnetometers and arrays of the invention can be used in a variety of magnetic-field detection functions and devices. The applications include biomagnetometry, particularly of the brain and heart, and measurement of non-animate subjects such as manufactured articles for flaws, objects that alter the magnetic field lines of the earth, and the earth itself.

The present invention represents an important breakthrough in the art of magnetometers, such as those used for for biomagnetometry. It also finds application in other fields such as the detection of magnetic flaws within materials. Other features and advantages of the invention will be apparent from the following more detailed description of the invention, taken in conjunction with the accompanying drawings, which illustrate, by way of example, the principles of the invention.

DETAILED DESCRIPTION OF THE PREFERRED EMBODIMENTS

Figure 1:
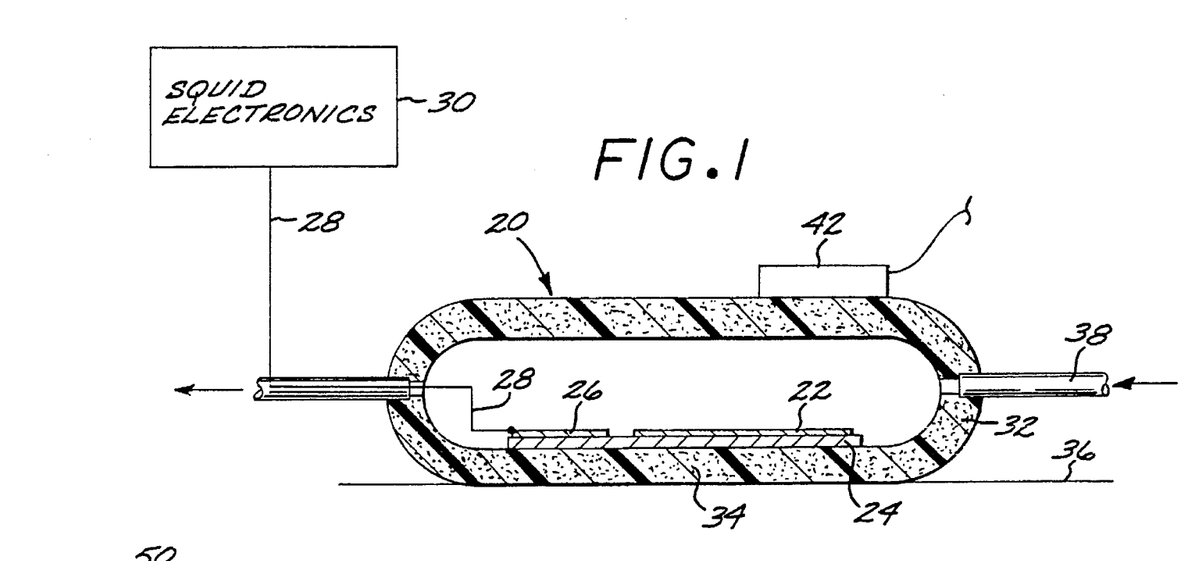
FIG. 1 is a side sectional view of a magnetometer utilizing a single pickup coil and SQUID detector.

A magnetometer 20 according to the present invention is illustrated in FIG. 1. The magnetometer includes a magnetic field pickup coil 22 made of a material having a superconducting critical temperature (Tc) of more than about 77 K. Any material having a superconducting critical temperature greater than about 77 K is operable. The pickup coil 22 may be a single coil with one or more loops, or a gradiometer having multiple loops in parallel planes, or any other operable configuration. (Some exemplary configurations will be discussed in greater detail in relation to FIGS. 4–6.) There may be a single pickup coil 22, or multiple pickup coils oriented to receive various components of a three-dimensional magnetic field. The pickup coil 22 may be formed from wire, but is more conveniently prepared as a patterned/etched thin film loop on a substrate 24, as illustrated.

The magnetometer 20 also includes a magnetic field detector 26 that receives electrical signals from the pickup coil 22 and produces an electrical detector output signal on a lead 28 responsive to the signal received by the pickup coil 22. The magnetic field detector 26 is made from a material having a superconducting critical temperature of more than about 77 K. Any material having a superconducting critical temperature greater than about 77 K is operable. The magnetic field detector 26 preferably includes a superconducting quantum interference device or SQUID, a well-known type of detector that includes one or two Josephson Junctions and can detect very small increments of current flow change in a circuit. There is a magnetic field detector 26 for each pickup coil 22. If multiple pickup coils are present, there is a magnetic field detector for each pickup coil. The magnetic field detector 2b may be supported on a separate support, but preferably is supported on the same substrate 24 as the pickup coil 22. The detector 26 is preferably made by thin-film techniques. The fabrication of thin-film pickup coils and detectors on a single substrate will be described subsequently.

The output signal from the magnetic field detector 26 is conveyed on the lead 28 to room-temperature SQUID electronics 30. The use of SQUIDs and their electronics 30 is well known in the art, and is described, for example, in U.S. Pat. Nos. 3,980,076, 4,079,730, 4,386,361, and 4,403,189, whose disclosures are incorporated by reference.

The pickup coil 22 and the magnetic field detectors 26, both preferably supported on a single substrate 24, are placed into the interior of an insulated enclosure 32. The insulated enclosure 32 is preferably a hollowed block of insulating foam, such as styrofoam, a polymer honeycomb, or any other material that has a low coefficient of heat transfer. The enclosure 32 may be coated with an impermeable coating such as the Vest Systems Model 105/205 two-part epoxy available from Gongcon, Inc., Bay City, Mich., to prevent the contact of coolant with the human subject being measured. The thickness of the foam is selected to be sufficient to maintain the pickup coil 22 and the magnetic field detector 26 in their superconducting states when the magnetometer 20 is operating, in conjunction with the available coolant. The foam also must be sufficiently thick, at least on a bottom 34 of the enclosure 32, that a surface 96 of the subject being studied or measured is not unduly chilled. Experience has shown that, if the interior of the enclosure 32 is cooled to liquid nitrogen temperature, 77 K, the thickness of the insulating foam should be at least about 1/8 inch thick. The insulating foam is preferably not made any thicker than necessary in the bottom 34 region of the enclosure 32, because increasing the thickness separates the pickup coil 22 from the surface 36 more than is necessary. In as much as the magnetic field falls off rapidly with increasing separation, it is desirable to make the spacing between the pickup coil and the surface 36 as small as possible. The enclosure 32 is preferably made in a split bottom/top form, so that the substrate 24 can be placed into the bottom, and the top sealed over the bottom with an adhesive or clamp. The size of the enclosure is determined by the required size of the pickup coil 22, and can be smaller than 1 inch on a side and ½ inch thick. Larger sizes are used if a larger pickup coil 22 is required to achieve greater sensitivity of the magnetometer.

The interior of the enclosure 32 is cooled by a stream of coolant introduced through a coolant supply line 38, and expended coolant is exhausted through a vent line 40. The lines 38 and 40 are readily provided by forcing a small fitting through the wall of the enclosure 32, and then attaching an external insulated line. The coolant is preferably a cryogenic gas such as gaseous nitrogen at a temperature near to the boiling point of liquid nitrogen, or liquid nitrogen itself. Other coolants can be used, as appropriate to the materials used in constructing the pickup coil 22 and the detector 26. Liquid or cryogenic gaseous nitrogen is preferred, because liquid nitrogen is inexpensive, readily available, non-explosive, has a relatively large heat of vaporization, and is the major component of the air. There is no concern with spills or evaporated gas entering the atmosphere.

Figure 10:
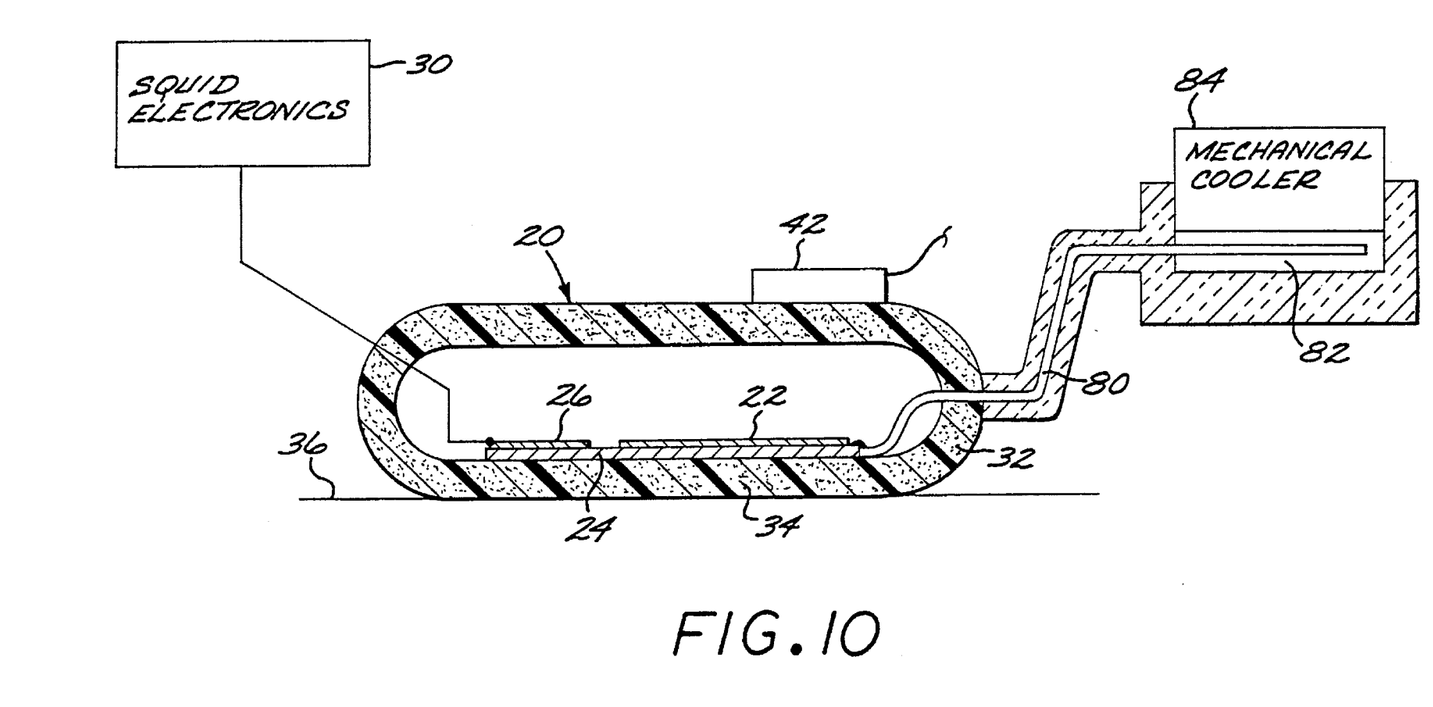
FIG. 10 is a diagrammatic view of a magnetometer utilizing an external mechanical cooler.

Another approach for cooling the magnetometer 20 is illustrated in FIG. 10. The construction of the pickup coil 22, substrate 24, field detector 26, enclosure 82, and related components is the same as illustrated in FIG. 1. Instead of cooling the interior of the enclosure 32 with liquid gas or a cryogenic gas, a thermally conductive path 80 such as an insulated braided copper wire extends from the interior of the enclosure 32 to an insulated thermal reservoir 82. The thermally conductive path 80 desirably contacts the substrate 24 directly, to provide a heat flow path from the pickup coil 22 and field detector 26. The thermal reservoir 82 is preferably a copper block that is cooled to a temperature below that required for the interior of the enclosure 92 by contact with liquid gas or a cryogenic gas, or by a closed cycle mechanical cooler 84 as depicted in FIG. 10. Such closed cycle mechanical coolers are well known in the art and commercially available. The mechanical cooler 84 could equivalently be used to cool the interior of the enclosure 92 directly, but the approach of FIG. 10 is preferred because it is easy to provide a number of thermally conductive paths extending from the single thermal reservoir to a number of magnetometer modules.

What is not included in the structure of the enclosure 92 is significant. There is no vacuum container structure within or made a part of the enclosure 22. A vacuum container structure is present in cryogenic enclosures or dewars when either the pickup coil or the detector is made of a low-To superconducting material having a critical temperature far below 77 K. In a typical prior approach, the pickup coil and detector are made at least in part of niobium, whose superconducting Tc is about 10 K. They are therefore cooled with liquid helium at a temperature of 4.2 K.

To maintain such a low temperature, a vacuum-insulated dewar is conventionally used. Maintenance of a vacuum and such a low temperature requires a heavy, complex insulating structure and necessitates the large size of conventional dewars and superconducting magnetometers. The structure of the dewar must be sufficiently thick and strong to support the weight of the dewar and liquid gas therein, and to support the pressure differential across the walls of the vacuum space. The thick structure therefore necessarily spaces the pickup coil some distance from the subject being measured. The necessity of a vacuum-insulated structure in prior superconducting magnetometer designs dictates that the entire magnetometer must be large, bulky, and heavy. The magnetometer is therefore more expensive and difficult to use than the present magnetometer, and places the pickup coil further from the subject than in the present design. Some examples of prior dewar constructions are described in U.S. Pat. Nos. 4,872,921 and 4,779,952, whose disclosures are incorporated by reference.

It is usually desirable to be able to establish the position of the magnetometer 20 very precisely. The position can be determined manually or optically, but is more preferably determined by an electromagnetic position measuring device of the type disclosed in U.S. Pat. No. 4,799,955, whose disclosure is incorporated by reference. In the magnetometer 20 of FIG. 1, a receiving unit 42 of the electromagnetic position measuring device is affixed to the outside of the enclosure 32. The position measurement is accomplished according to the approach disclosed in the '355 patent.

Figure 2:
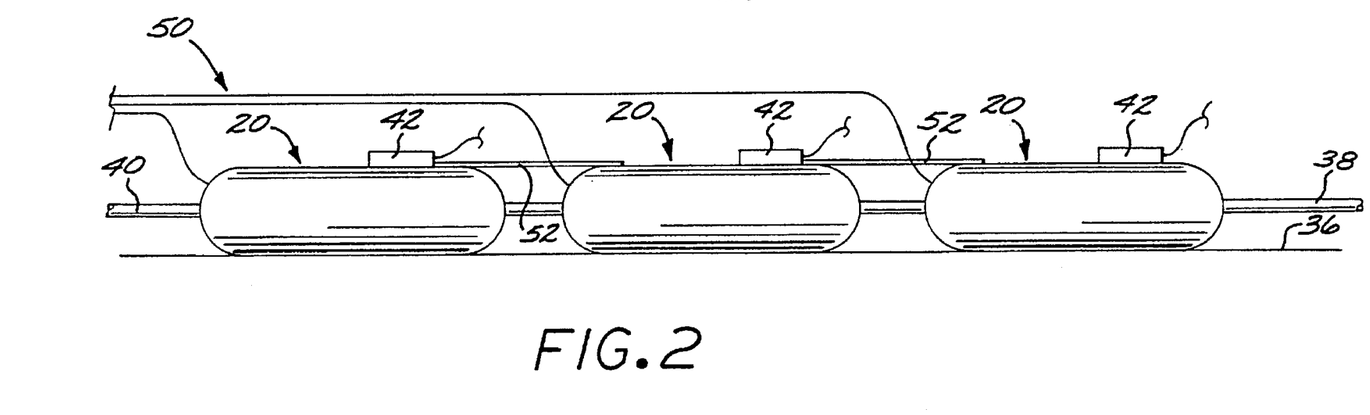
FIG. 2 is an elevational view of several of the magnetometers of FIG. 1 arranged in an array.

The magnetometer 20 may be used by itself, or may be Joined with other similar magnetometers to form an array 50, shown in FIG. 2. The several magnetometers 20 of the array 50 may be conveniently joined by connectors 52. The connectors 52 may be straps or some other flexible material, so that the array 50 is segmented and flexible. The connectors 52 may be a rigid plastic or other material, so that the array 50 is a rigid array. FIG. 2 depicts coolant supply lines 38 and 40 arranged so that coolant flows through the magnetometers 20 in a serial fashion. Alternatively, the coolant lines may be arranged so that the coolant flows through the magnetometers in a parallel fashion. A thermally conductive path cooling approach such as that of FIG. 10 may also be used.

Figure 3:
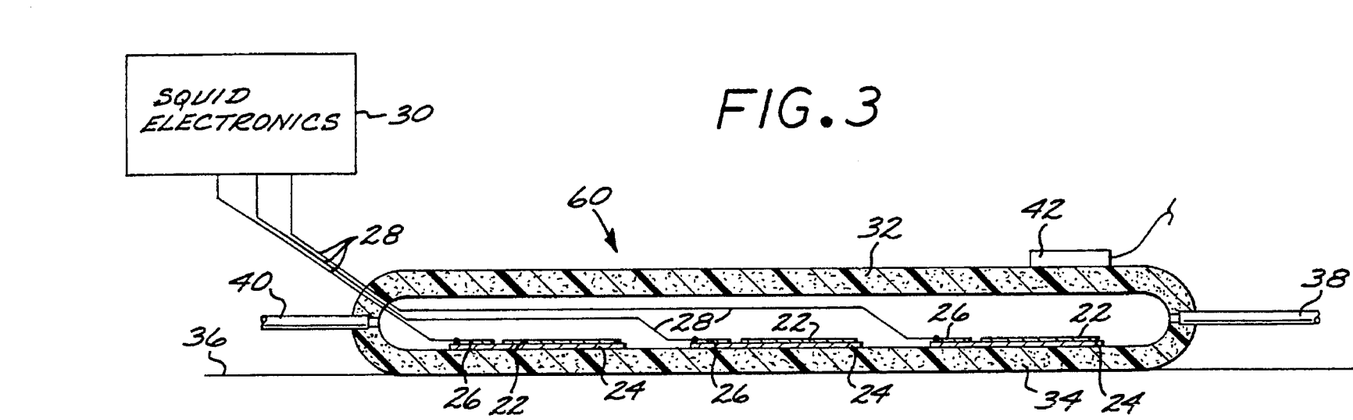
FIG. 3 is a side sectional view of a magnetometer utilizing more than one pair of pickup coils and SQUID detectors in a single enclosure.

Another embodiment of the invention is shown in a magnetometer 60 of FIG. 8. In this embodiment, the construction of the enclosure 32 and related structure is similar to that of the enclosure of FIG. 1, and the same reference numerals have been used in FIG. 3 as in FIG. 1. The principal difference is that at least two, and preferably more, sets of pickup coils 22 and magnetic field detectors 26, each set mounted on its own substrate 24, are mounted within the interior of the enclosure 32.

The design and fabrication of pickup coils and SQUIDS are widely known in the superconductivity field. One preferred embodiment of the pickup toll 22 (In this case a two-turn planar toll) and magnetic field detector 26 on the substrate 24 are shown in more detail in FIG. 4. The pickup coil 22 and magnetic field detector 26 are preferably made from the high-Tc superconductor $YBa_2 Cu_3 O_{7-x}$ (where x is chosen so that the compound is superconducting, and typically is about 0.15) deposited on a substrate of $LaAlO_3$, yttrium-stabilized $ZrO_3$, or $SrTiO_3$. Other operable superconductors and substrates may be used. As additional high-Tc super conductors with lower cooling requirements are discovered, it should be possible to make the walls of the enclosure even thinner, and use other coolants when desired.

Operable detectors of this material have been fabricated and are known in the art, see for example the publications of M. S. DiIorlo et al., "Practical high Tc Josephson Junctions and dc SQUIDS operating above 85 K", Appl. Phys. Lett., Vol. 58 (22), pages 2552–2554 (June 1991); J. Gao et al., "Controlled preparation of all high-To SNS-type edge Junctions and DC SQUIDS", Physica C, Vol. 171, pages 126–130 (1990); R. Gross et al., "Low noise $YBa_2Cu_3O_{7-x}$ grain boundary Junction dc SQUIDs", Appl. Phys. Lett., vol. 57(7), pages 727–729 (August 1990); and K. P. Daly et al., "Substrate step-edge $YBa_2Cu_3O_7$ rf SQUIDs", Appl. Phys. Lett., vol. 58 (5), pages 548–545 (February 1991).

In the approach of DiIorio et al., for example, to produce a SQUID an inclined step is etched in a $LaAlO_3$ crystalline substrate. A 50–150 nanometer thick layer of an appropriate superconduct or such as $YBa_2Cu_3O_{7-x}$ superconductor is deposited on the substrate by off-axis magnetron sputtering. A layer of normal metal, such as silver, up to about 600 nanometers thick is deposited over the superconductor layer. The structure is patterned by standard photolithography to form the SQUID. Additionally, the superconductor may be simultaneously patterned to form a conductive path in the desired form of the pickup coil, such as the pickup coil 22 of FIG. 4. The weak-link Junctions of the detector 26 are formed at the step in the substrate.

Figure 4:
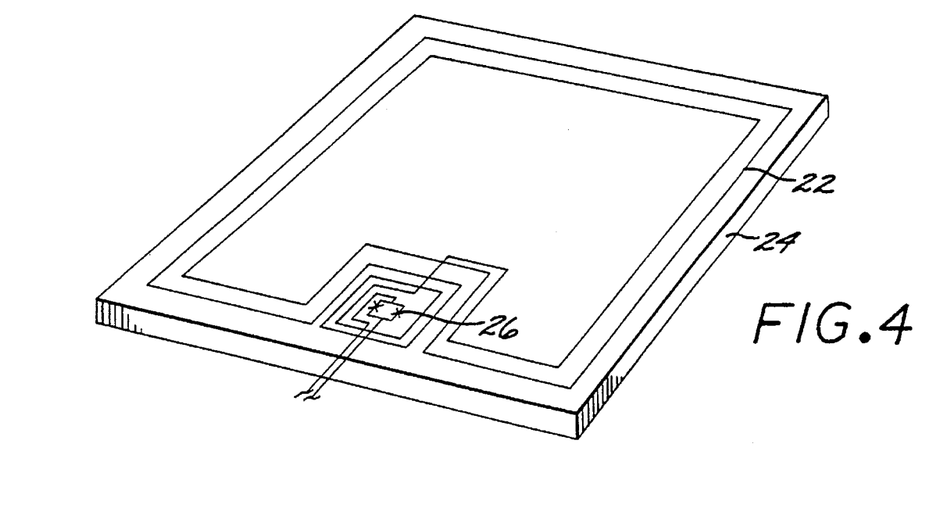
FIG. 4 is a perspective view of one configuration of a planar magnetometer pickup coil and SQUID on a substrate.
Figure 5:
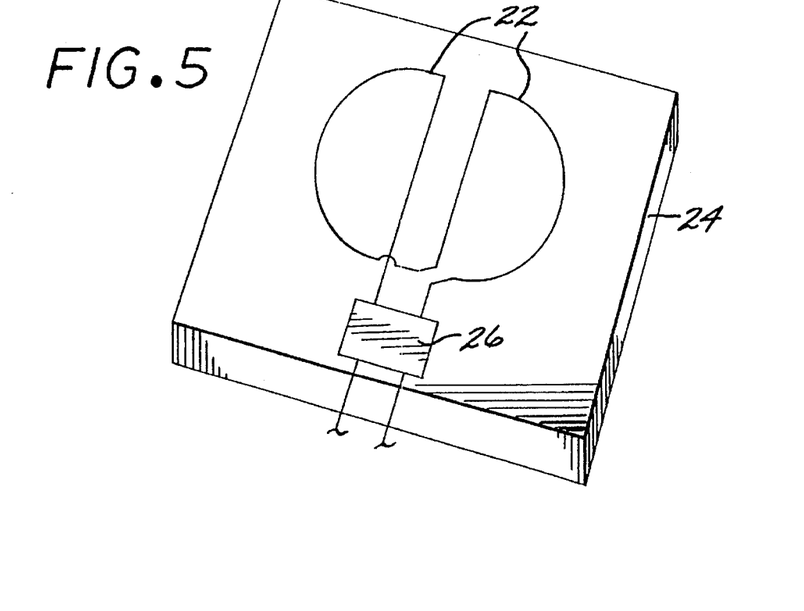
FIG. 5 is a perspective view of a gradiometer and SQUID on a substrate.
Figures 6, 7:
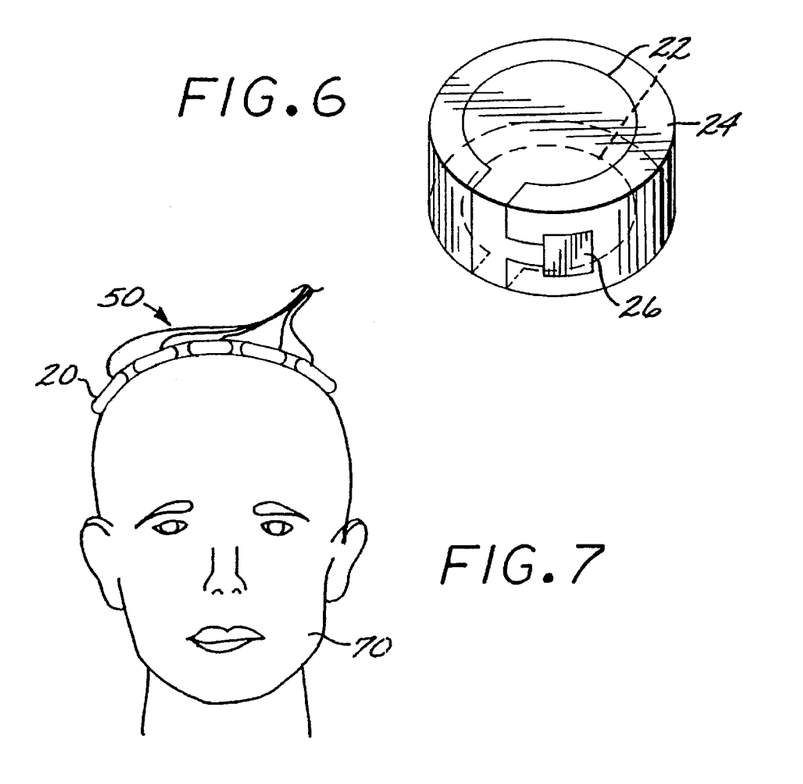
FIG. 6 is a perspective view of a gradiometer Formed of planar magnetometers on parallel planes, and a SQUID.
FIG. 7 is an elevational view of a magnetometer array used to detect magnetic signals produced by the brain.

The pickup coil 22 can be arranged in any required form. FIG. 4 illustrates a planar magnetometer pickup coil. FIGS. 5 and 6, whose elements are indicated with the same identifiers as in FIG. 4, illustrate two other configurations. The pickup coil 22 of FIG. 5 is a planar gradiometer pickup coil. The pickup coil 22 of FIG. 6 is a three-dimensional gradiometer pickup coil. In each case, the pickup coil 22 and field detector 26 are mounted on the substrate 24. Another form of gradiometer can be constructed with two of the planar gradiometers of FIG. 4, one over the other. The present invention permits the use of all operable pickup coils that will fit within the enclosure 82, and are collectively termed "pickup coils" herein. Thus, the term "magnetometer" as used herein includes planar magnetometers and gradiometers.

Figure 8:
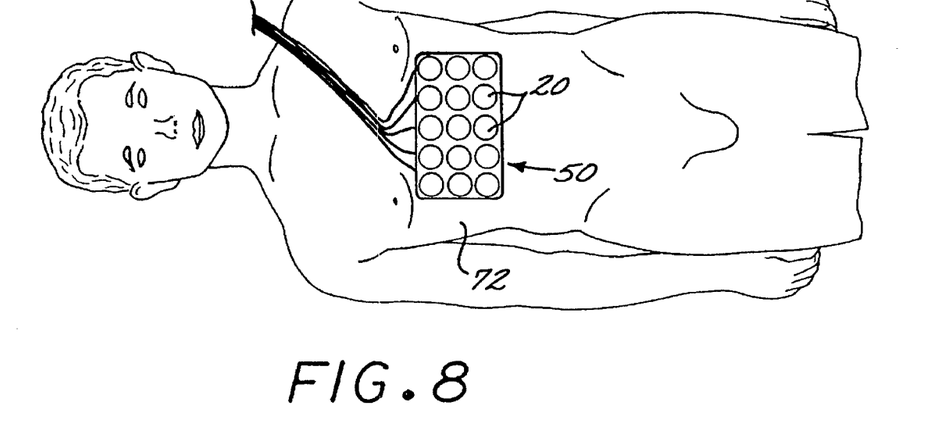
FIG. 8 is a plan view of a magnetometer array used to detect magnetic Signals produced by the heart.

The present invention can be used in a variety of applications, such as biomagnetometry. FIG. 7 illustrates an array 50 placed over a head 70 of a human subject, to measure magnetic fields produced by the brain. FIG. 8 illustrates an array 50 placed over a chest 72 of a human subject, to measure magnetic fields produced by the heart.

Figure 9:
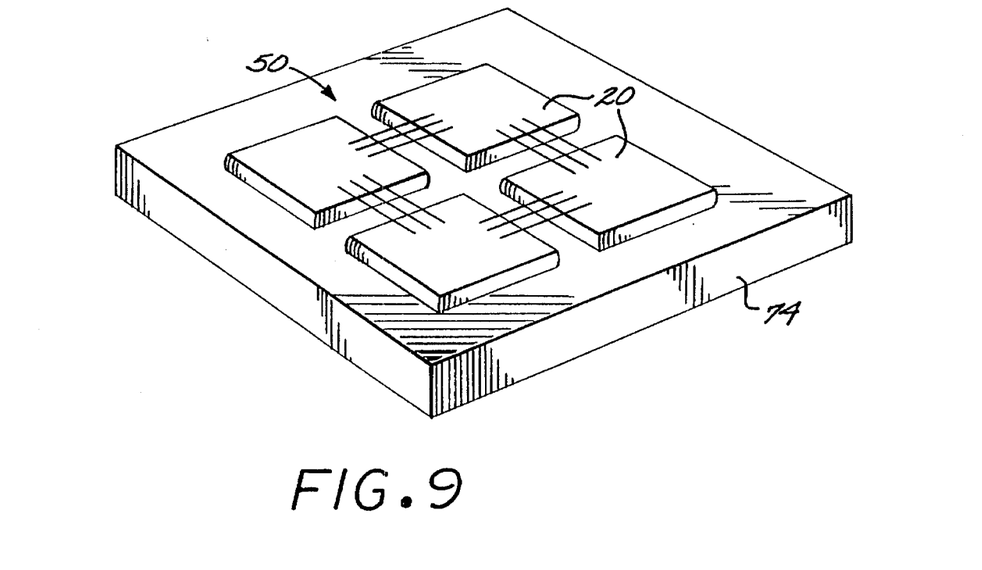
FIG. 9 is a perspective view of a magnetometer array used to measure a non-animate object, such as a piece of material.

Another type of application is in measurement of magnetic fields produced by the earth, machinery, or inert objects. FIG. 9 illustrates one example of the many non-biomagnetometry applications of the present invention, a non-destructive testing system. A single magnetometer 20 of the type discussed previously, or, as illustrated, an array 50 of the magnetometers 20, is placed adjacent to a piece of material 74 to be inspected for internal flaws or discontinuities that alter the magnetic field pattern. Such studies can be done with conventional magnetometers, but the magnetometer and array of the present invention provide an important advance in reducing the size and distance from the piece 74 to the pickup coil. Moreover, the present invention makes the entire approach more practical, because a fragile, bulky, heavy vacuum insulation system is not present to house the superconducting elements.

The approach of the invention provides a major advance in the art of superconducting magnetometers. A small, lightweight, portable superconducting magnetometer module is formed of high-Tc materials so that it can be maintained superconducting without a vacuum-insulated enclosure. Although particular embodiments of the invention have been described in detail for purposes of illustration, various modifications may be made without departing from the spirit and scope of the invention. Accordingly, the invention is not to be limited except as by the appended claims.

What is claimed is:

1. A magnetometer, comprising a magnetic field pickup coil;

a magnetic field detector that receives electrical signals from the pickup coil and produces an electrical detector output responsive thereto, wherein the pickup coil and the magnetic field detector are supported on a single substrate; and an insulated enclosure that encloses the pickup coil and the field detector and separates the pickup coil and the field detector from an external ambient temperature environment, the insulated enclosure having no vacuum insulation structure, and wherein the insulated enclosure has a flat bottom made, at least in part, of a foamed polymer, with the single substrate having the pickup coil and magnetic field detector thereon located adjacent to the flat bottom and with the plane of the pickup coil oriented parallel to the flat bottom.

2. The magnetometer of claim 1, wherein the magnetic field pickup coil is made of a material having a superconducting critical temperature of more than about 77 K.

3. The magnetometer of claim 1, wherein the magnetic field detector is made of a material having a superconducting critical temperature of more than about 77 K.

4. The magnetometer of claim 1, wherein the magnetic field detector includes a superconducting quantum interference device.

5. The magnetometer of claim 1, further including means for cooling the interior of the insulated enclosure.

6. The magnetometer of claim 5, wherein the means for cooling includes a mechanical cooler located outside the Insulated enclosure.

7. The magnetometer of claim 1, further including means for establishing the position of the insulated enclosure, the means for establishing being affixed to the Insulated enclosure.

8. The magnetometer of claim 1, wherein the interior of the insulated enclosure is no larger than required to receive the single substrate therein.

9. The magnetometer of claim 1, wherein the pickup coil is a planar magnetometer.

10. The magnetometer of claim 1, wherein the pickup coil is a gradiometer.

11. A magnetometer, comprising at least two magnetometer modules arranged in an array, each magnetometer module having at least one magnetic field pickup coil, at least one magnetic field detector, each magnetic field detector receiving an electrical signal from one of the pickup coils and producing an electrical detector output responsive thereto, and an insulated enclosure that encloses the at least one pickup coil and its field detector, the insulated enclosure having no vacuum insulation structure; and means for mechanically interconnecting the magnetometer modules of the array.

12. The magnetometer of claim 11, wherein the magnetic field pickup coil of each module is made of a material having a superconducting critical temperature of more than about 77 K.

13. The magnetometer of claim 11, wherein the magnetic field detector of each module is made of a material having a superconducting critical temperature of more than about 77 K.

14. The magnetometer of claim 11, further including means for establishing the position of the insulated enclosure affixed to the insulated enclosure.

15. The magnetometer of claim 11, wherein the insulated enclosure of each module is made at least in part of a foamed polymer.

16. The magnetometer of claim 11, further including means for providing a coolant to the interior of the insulated enclosure of each module.

17. The magnetometer of claim 11, wherein each insulated enclosure has a flat bottom, and the plane of the pickup coil is oriented parallel to the flat bottom.

18. A magnetometer, comprising means for picking up and detecting magnetic fields, the means being made entirely of materials having superconducting critical temperatures of more than about 77 K, the means for picking up and detecting including a magnetic field pickup coil and a magnetic field detector;

a generally flat insulated enclosure that encloses the means for picking up and detecting, wherein the insulated enclosure has a flat bottom, is made of a foamed polymer, and has no vacuum insulation structure, and wherein the magnetic field pickup coil is supported on a substrate that is located adjacent to and oriented parallel to the flat bottom of the insulated enclosure; and means for providing a coolant to the interior of the insulated enclosure.

19. The magnetometer of claim 11, wherein the means for mechanically interconnecting includes a connector made of a flexible material.

20. The magnetometer of claim 11, wherein the means for mechanically interconnecting includes a connector made of a rigid material.

21. The magnetometer of claim 1, wherein the bottom of the insulated enclosure is about 1/8 inch thick.

* * * * *